United States Patent [19]
Sorenson et al.

[11] Patent Number: 5,840,283
[45] Date of Patent: Nov. 24, 1998

[54] COMPOSITION AND METHOD FOR TREATING DISEASED NAILS

[75] Inventors: James L. Sorenson, Salt Lake City; Robert V. Petersen, Murray, both of Utah

[73] Assignee: Sorenson Pharmaceutical, Inc., Salt Lake City, Utah

[21] Appl. No.: 921,771

[22] Filed: Aug. 15, 1997

Related U.S. Application Data

[63] Continuation of Ser. No. 528,302, Sep. 14, 1995, abandoned.

[51] Int. Cl.⁶ ............................ A61K 7/04; A61K 38/43
[52] U.S. Cl. .................... 424/61; 424/405; 424/94.64; 424/94.65; 514/946
[58] Field of Search ...................... 424/61, 94.65, 424/94.64, 405; 514/946

[56] References Cited

U.S. PATENT DOCUMENTS

| | | | |
|---|---|---|---|
| 2,917,433 | 12/1959 | Goldman | 167/65 |
| 3,493,652 | 2/1970 | Hartman | 424/94 |
| 4,122,158 | 10/1978 | Schmitt | 424/27 |
| 4,226,854 | 10/1980 | Klein et al. | 424/94 |
| 4,361,551 | 11/1982 | Galbraith | 424/94 |
| 4,567,044 | 1/1986 | DeSantis | 424/94 |
| 4,668,228 | 5/1987 | Bolton et al. | 523/111 |
| 4,820,711 | 4/1989 | Pearlman | 514/274 |
| 4,820,720 | 4/1989 | Sanders et al. | 424/449 |
| 4,917,676 | 4/1990 | Heiber et al. | 424/449 |
| 5,024,838 | 6/1991 | Parrilla | 424/443 |
| 5,156,846 | 10/1992 | Petersen et al. | 424/443 |
| 5,206,026 | 4/1993 | Sharik | 424/445 |
| 5,296,222 | 3/1994 | Petersen et al. | 424/94.63 |
| 5,465,735 | 11/1995 | Patel . | |

FOREIGN PATENT DOCUMENTS 2556218  6/1985  France .

*Primary Examiner*—Edward J. Webman
*Attorney, Agent, or Firm*—Trask, Britt & Rossa

[57] ABSTRACT

A nail-permeable medication means is disclosed for delivering a medicament through nails, claws, hoofs, or other similar hardened tissue of dermal derivation. The nail-permeable medication means includes a proteolytic enzyme component which facilitates permeation of substances through the hardened nail or keratin tissue, and also includes a medicament component selected to treat a specific disease. The nail-permeable medication means is particularly useful for treating onychomycosis of the fingernail or toenail, and avoids the need for more drastic therapeutic modalities, such as removal of the nail.

12 Claims, 10 Drawing Sheets

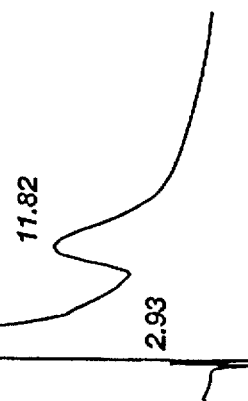
Fig. 12
Fig. 11

COMPOSITION AND METHOD FOR TREATING DISEASED NAILS

This application is a continuation of application Ser. No. 08/528,302, now abandoned filed Sep. 14, 1995.

BACKGROUND

1. Field of Invention

This invention relates to the medical treatment of diseased nails, claws or hoofs (i.e., unguis), and specifically relates to the treatment of diseased nails by facilitating penetration of medication through the nail.

2. Statement of the Art

Humans and animals alike are commonly plagued by the infiltration of micro-organisms beneath the nail, claw or hoof which results in a disease condition causing pain, discoloration, and frequently loss of the unguis. In humans, for example, some diseases which attack the nail or nail bed can be treated fairly successfully with the use of cleansing and/or antiseptic preparations, while other diseases require treatment by such means as systemic drug therapy. Nonetheless, many disease conditions of the nail, particularly onychomycosis (i.e., fungal diseases), have had a relatively low success rate for treatment due to the intransigent nature of the infectious micro-organisms.

It has been estimated that greater than twenty percent (20%) of the population of the United States over the age of 40 suffers from onychomycosis of the fingernails or toenails. The disease is known to occur to a lesser extent in people below the age of forty, but the occurrence of disease is still significant. Unfortunately, the current modalities for treatment of onychomycosis show a very low success rate.

Common means of treating microbial diseases, including onychomycosis, include oral administration of drugs and laser therapy. Laser therapy, as yet, is not well-developed nor widely practiced, and is very expensive because it must be conducted in a doctor's office by a trained technician. Systemic drug therapy through oral administration has also proven to be relatively unsuccessful because of drug intolerances, the expense of the medications and low patient compliance.

The most common means of treating onychomycosis is to remove the nail completely and topically apply medication to the underlying nail bed. However, not only is such treatment cosmetically unsightly, but the fungus which invades the nail often remains in the matrix of the finger or toe (where the nail is formed) and the disease reoccurs immediately upon, or during, ingrowth of the new nail.

Undoubtedly, treatment of diseases involving nails would be greatly enhanced by the ability to access the area around and below the nail, as well as to penetrate the nail itself, without having to remove the nail. However, the thick and/or hardened nature of nails renders access through, and to the area below, the nail very difficult. The same can be said of diseases involving the claws or hooves of animals.

The usefulness of antifungal drugs in treating onychomycosis has been limited heretofore because of resistance to penetration of the nail or because of limited access to the nail bed through the nail. Thus, it would be an improvement in the art to provide means for enhancing penetration of the nail so that treatment of the nail with medication may occur at the situs and without having to remove or otherwise significantly damage the nail. It would also be advantageous to provide such penetration means at a reasonable cost to the consumer, and in a form which would facilitate and encourage proper and consistent self-use by the afflicted person.

The art has disclosed the use of various substances as permeation facilitators in drug delivery systems, but such permeation enhancers have only been used in connection with permeation of the epidermis. Examples of such methods and systems have been disclosed in U.S. Pat. No. 5,156,846; U.S. Pat. No. 5,296,222; French Patent Publication No. 2,448,903; and French Patent Publication No. 2,556,218. The permeation of thickened nails, or other unguis, presents unique difficulties not encountered in permeation of the epidermis. To date, no means have been developed to enhance permeation of nails for effective treatment of diseases involving nails, or other unguis.

SUMMARY OF THE INVENTION

In accordance with the present invention, nail-permeable medication means are provided for facilitating the penetration of nails, claws, hoofs, or other hardened tissue derivatives of the skin or dermis, with appropriate medicaments to promote treatment of disease conditions which originate or exist, in whole or in part, in or below the hardened tissue form. The nail-permeable medication means of the present invention is applicable to many types and forms of hardened tissue, as described above, but use of the invention on the human nail is described hereinafter as an exemplar.

The nail-permeable medication means of the present invention comprises an effective amount of an enzymatic composition, in sufficient concentration to modify the tissue structure of the nail to enhance permeation of a medicament therethrough, and an effective amount of medicament. The enzymatic composition contains a proteolytic enzyme selected to be capable of temporarily modifying the cellular structure of the nail in a manner to permit permeation of medication through the nail without permanently harming (e.g., denaturing, degrading or destroying) the structural integrity of the nail. The proteolytic enzyme preferably may be selected from the group comprising papain, bromelain, chymotrypsin, trypsin, or combinations thereof. However, other proteolytic enzymes may be equally suitable. Other substances may be added to the proteolytic enzyme in formulating the enzymatic composition, including activators, solubilizers, buffering agents, chelating agents, preservatives, thickening agents, colorants, permeation facilitators, etc. Water may or may not be a component of the enzymatic composition. Commercially available formulations containing proteolytic enzymes in an appropriate concentration, such as Sorenzyme™ (Sorenson Pharmaceutical, Inc.) or Panafil® (Rystan Company), may be suitable for use in the invention.

The nail-permeable medication means also includes a medicament which is especially selected for treatment of a particular disease condition. The concentration of medicament in the nail-permeable means is sufficient to effectively control or eliminate the disease condition. Any medicament may be used in the invention provided that the medicament does not react adversely with the proteolytic enzyme to render either the enzymatic component or the medicament ineffective in facilitating permeation of the nail-permeable medication means through the nail. It is notable in that respect that many medications have a water base, or have a water component in addition to certain activators (e.g. thiols and mercaptans which include cysteine and a chelating agent, such as EDTA [ethylenediaminetetraacetic acid]) which, when admixed with the enzymatic composition, may begin to degrade the enzyme and/or reduce its effectiveness. However, admixture of a water-based or water-containing medicament with a proteolytic enzyme will typically degrade the enzymatic component slowly enough that significant penetration of the nail still takes place and the medicament is successfully delivered to the disease site. Generally, papain and other proteolytic enzymes are effective for approximately twenty-four hours after mixture with water where certain activators are present. In the absence of such activators, papain may remain active for up to two years.

Examples of drugs which may be used in the nail-permeable medication means include antibacterial, antiviral, antifungal and other antimicrobial compositions. Such drugs may also be ionic, anionic, nonionic, cationic, zwitterionic, or ampholytic. Suitable drugs for use in the nail-permeable medication means include ciclopirox olamine, miconazole, tolnaftate, terbinafine, amorolfin and econazole, as well as other drugs. It is possible to use pure forms of such drugs in forming the nail-permeable medication means or commercial preparations of such drugs (e.g. in cream or lotion form) may be used.

The nail-permeable medication means is applied to a nail infected with a disease condition by bringing into contact with the nail the proteolytic enzyme composition and the selected medicament. The nail and surrounding area is preferably first cleaned. Additionally, the nail may be filed or sanded and/or may be moistened for a short while before application, depending on the thickness or horniness of the nail, to enhance penetration of the medicament therethrough. In most instances, the nail will be moist anyway because of the wearing of socks or other foot coverings. The nail-permeable medication means is maintained in contact with the affected nail for a period sufficient to permit penetration of the enzymatic component and medicament through the nail. The period of contact may typically be twenty-four hours. During that time the treated area may be preferably occluded.

The separate enzymatic component and medicament component may preferably be admixed together at a ratio of from about 25:75 to 75:25, with a preferred ratio of about 50:50. The separate components may preferably be admixed together immediately before application to the nail. Alternatively, the two components may preferably be premixed, provided that the addition of the medicament to the enzymatic component does not appreciably degrade the enzymatic component. The process of admixing the components and applying them to the affected nail area may be repeated as necessary and as permitted by the safety and efficacy indications of the drug and the enzymatic component.

The means of delivering the nail-permeable medication means to the diseased nail area may be accomplished in several manners. As a commercial tool to most conveniently package the components, and to accurately measure for the user the correct amount of components, a system may be used which comprises a first compartment containing the proteolytic enzyme component in a pre-measured amount, a second compartment containing a pre-measured amount of the appropriate medicament component, and an intervention means between the two compartments which enables a combination of the component from one compartment and the contents of the other compartment for mixing. The compartment in which the mixing of the components takes place may also have an opening which permits the admixture to be squeezed from the compartment onto the affected area. Occlusion means may also be associated with the two-compartment system for occluding the nail area to which the permeable medication means has been applied.

BRIEF DESCRIPTION OF THE FIGURES

FIG. 11 is a computer-identified and quantified sample peak;

FIG. 12 is an unidentified peak in the expected location for ciclopirox olamine.

DESCRIPTION OF THE PREFERRED EMBODIMENT OF THE INVENTION

The nail-permeable medication means is comprised of a proteolytic enzyme component and a medicament component. The proteolytic enzyme component of the nail-permeable medication means acts to modify the nail to facilitate penetration of the medicament through the nail. The proteolytic enzyme component includes a proteolytic enzyme such as papain, bromelain, chymotrypsin, or other suitable proteolytic enzymes, or combinations thereof. Papain may be a particularly suitable enzyme for inclusion in the nail-permeable medication means. The proteolytic enzyme component may also include substances which enhance the effectiveness of the proteolytic enzyme, including enzyme activators such as cysteine, and permeation facilitators such as urea. The proteolytic enzyme component may also include various other materials which render the nail-permeable medication means effective for penetrating the nail, including one or more alcohols. Water may be included in the proteolytic component.

The amount or concentration of enzyme in the proteolytic enzyme component is sufficient to facilitate penetration of medication into and through the nail, but is not so great that the nail tissue is irreparably damaged (i.e., will not rejuvenate or regenerate). In other words, it is well-known that proteolytic enzymes in higher concentration can cause various degrees of damage to skin tissue. In fact, proteolytic enzymes in higher concentrations are used to debride necrotic tissue in burn patients. However, the appropriate amount of proteolytic enzyme in the nail-permeable medication means must be particularly selected to permit permeation through the hardened keratin tissue, the significant constituent of nails, without resulting in irreparable damage to the nail.

Keratin is a protein formed by regularly repeated groupings of amino acids which form long chains. The chains are held together by lateral bonds, including acid-base, hydrogen and van derWaals and disulfide bonds. The exact mode or action of proteolytic enzymes on the keratin molecule of nails is not completely understood, but it appears that proteolytic enzymes affect the bonds of the keratin molecules. Hydration of the nail may also modify the keratin structure, such as by swelling. Absorbance spectrum studies were conducted on sample human toe nails to better understand the absorbance of papain and papain-based proteolytic enzyme compositions on such nails.

Figure 1:
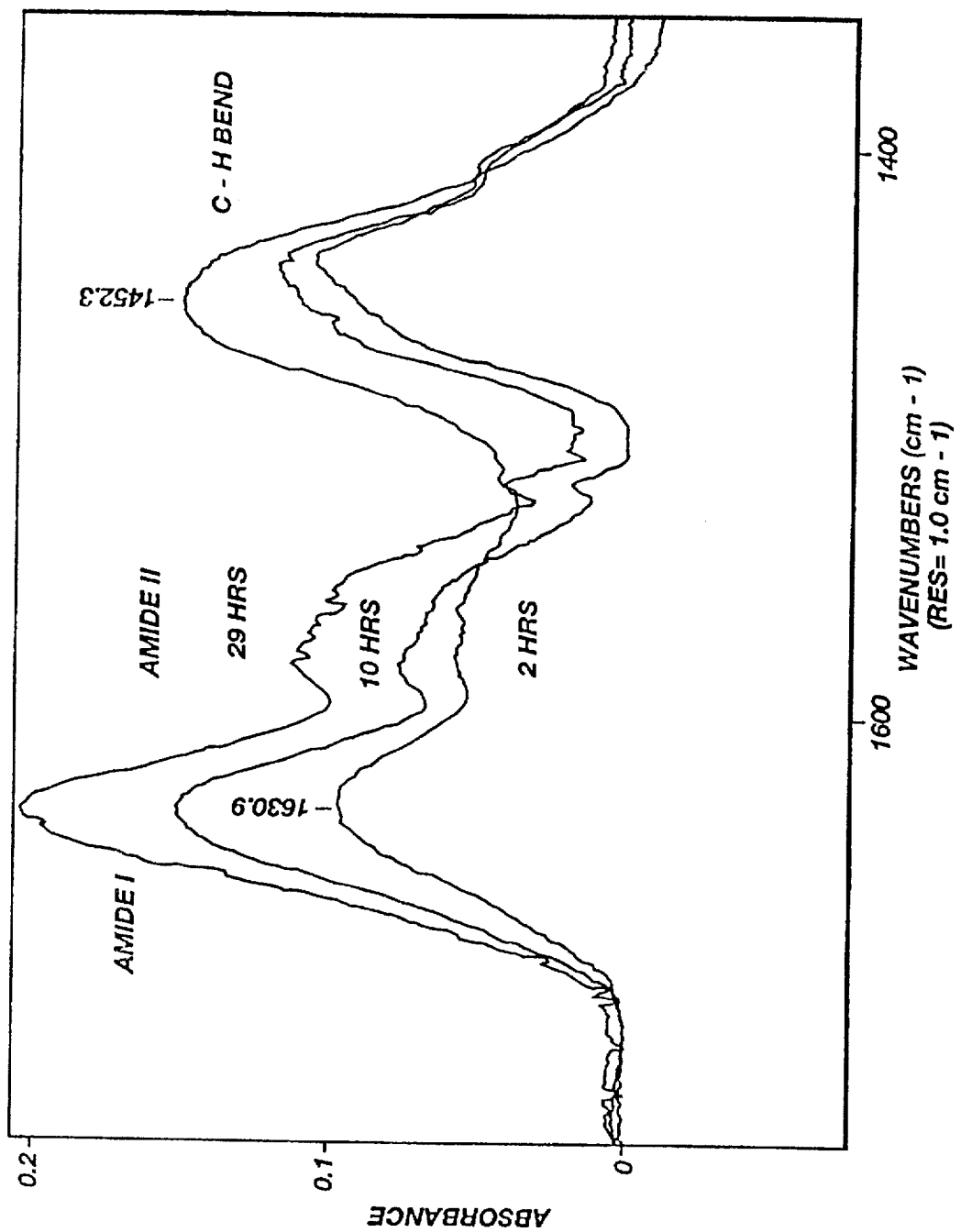
FIG. 1 is an absorbance spectrum of a first human toe nail sample which was hydrated in heavy water and scanned over a twenty hour period.
Figure 2:
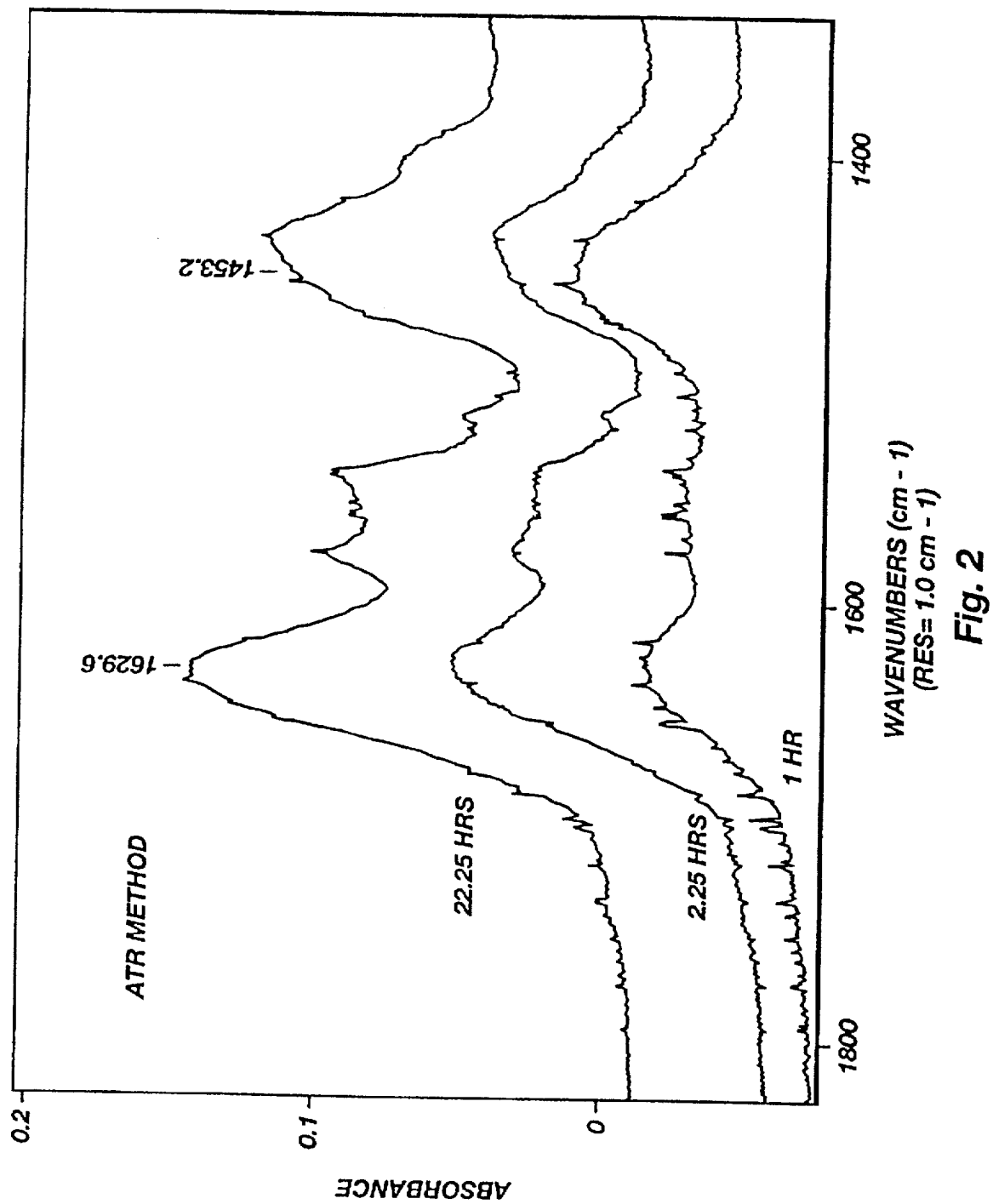
FIG. 2 is an absorbance spectrum of a second human toe nail sample which was hydrated in heavy water and scanned over a twenty-two hour period.
Figure 3:
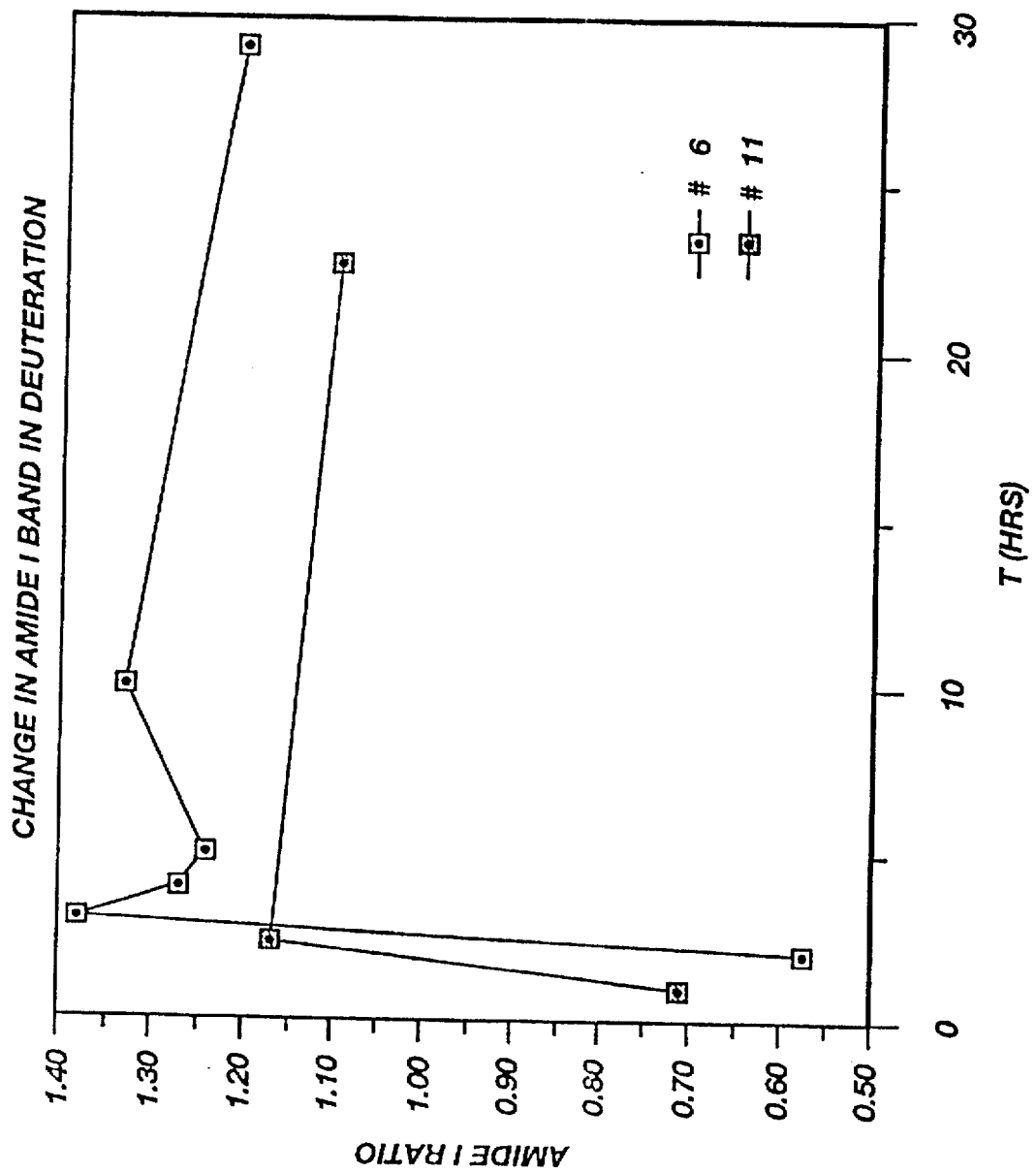
FIG. 3 is a chart of ratios of C=O bond stretching and C—H bond bending calculated from scanning information derived from hydrated human toe nails from the first human toe nail sample and from the second human toe nail sample.

The toe nails were placed under vacuum ($10^{-4}$ Torr) for five days to desiccate the samples, and were stored in sealed vials with a desiccant until used. The nails were then hydrated, using heavy water ($D_2O$), for up to twenty-nine hours. Various spectra on the nails were obtained thereafter as a function of time. FIG. 1 illustrates a spectrum obtained on a first deuterated toe nail, and FIG. 2 illustrates a spectrum obtained on a second deuterated toe nail. The amide I band (center of gravity) increased in intensity (absorbance) within two hours, and then remained constant (FIGS. 1 and 2). The spectrum did not exhibit further alterations in bandwidth, presence or absence of deconvoluted underlying bands or other spectral alterations as a function of time, confirming that hydration alone does not result in conformational alterations. The amide I center of gravity (1631 $cm^{-1}$ [C=O stretching]) compared to the C—H bending (1453 $cm^{-1}$) increased within two hours and then remained constant, as shown in FIG. 3, indicating that hydration occurred in approximately two hours.

Figure 4:
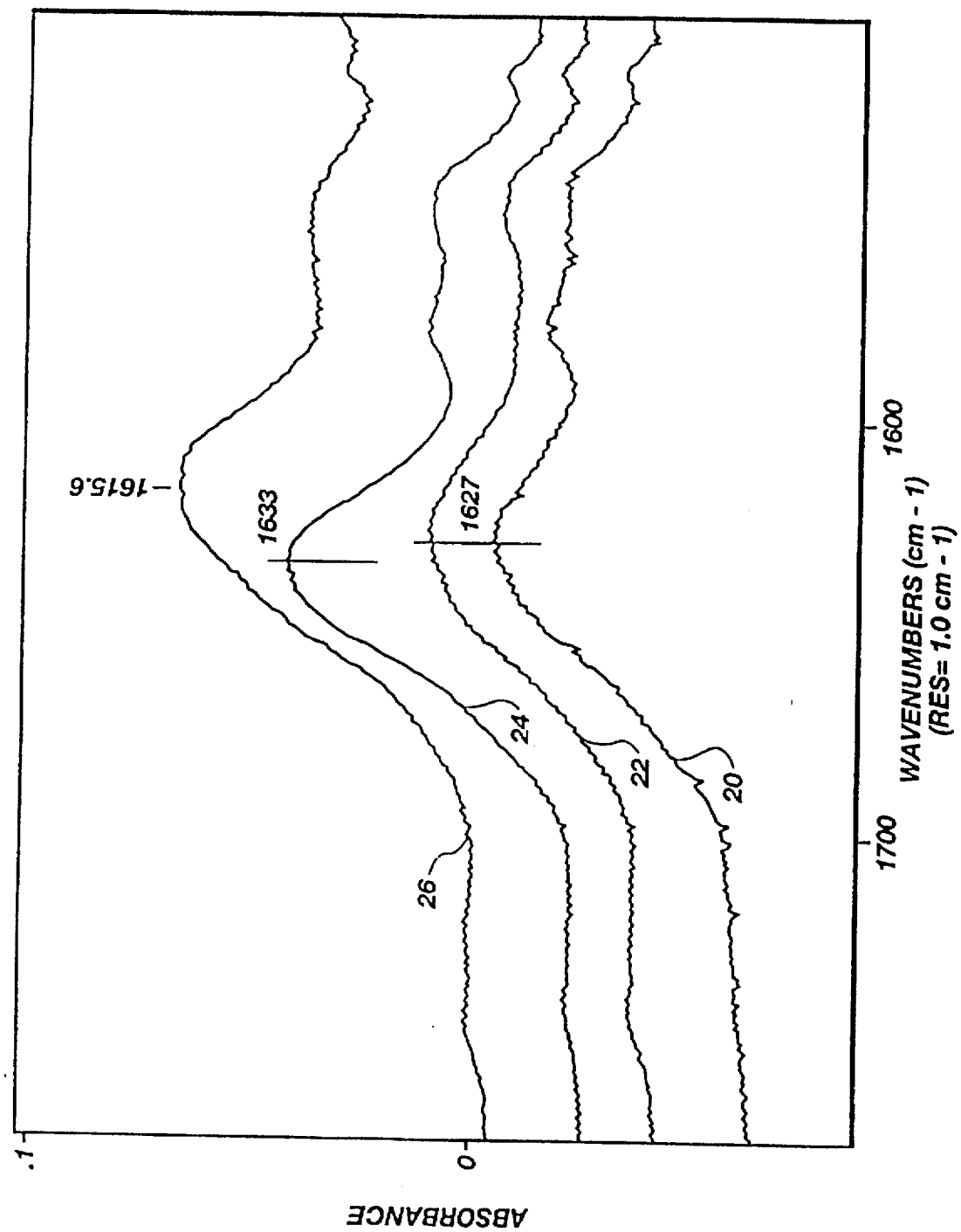
FIG. 4 is an absorbance spectrum of a human toe nail sample to which was applied varying amounts of a proteolytic enzyme composition.

Absorbance spectra were then obtained on hydrated toe nails to which was applied a papain or papain-based proteolytic enzyme composition for a period of three hours each. Toe nails were hydrated in heavy water for three hours. Various spectra were then obtained. FIG. 4 illustrates the comparative spectrum of a toe nail, beginning with a baseline spectrum 20 of the hydrated nail. FIG. 4 also illustrates a spectrum 22 of the hydrated nail to which was applied one milligram of a proteolytic enzyme composition containing six percent (6%) by weight papain (Marcor 30,000 USP units/mg, or equivalent activity), ten percent (10%) by weight urea, fifty-two percent (52%) by weight water and six percent (6%) by weight propylene glycol. A third spectrum 24 is plotted on the hydrated nail to which was applied three milligrams of the same proteolytic enzyme composition and a fourth spectrum 26 to which was applied an amount in excess of three milligrams of the same proteolytic enzyme composition. A shift in the amide I band suggested a redistribution or modification of α-helical conformations of the keratin, perhaps at the expense of β-conformations. A shift in the amide I band with excess application of the proteolytic enzyme composition suggests a substantial increase in random β-conformations at the expense of α-helical conformations.

Figure 5:
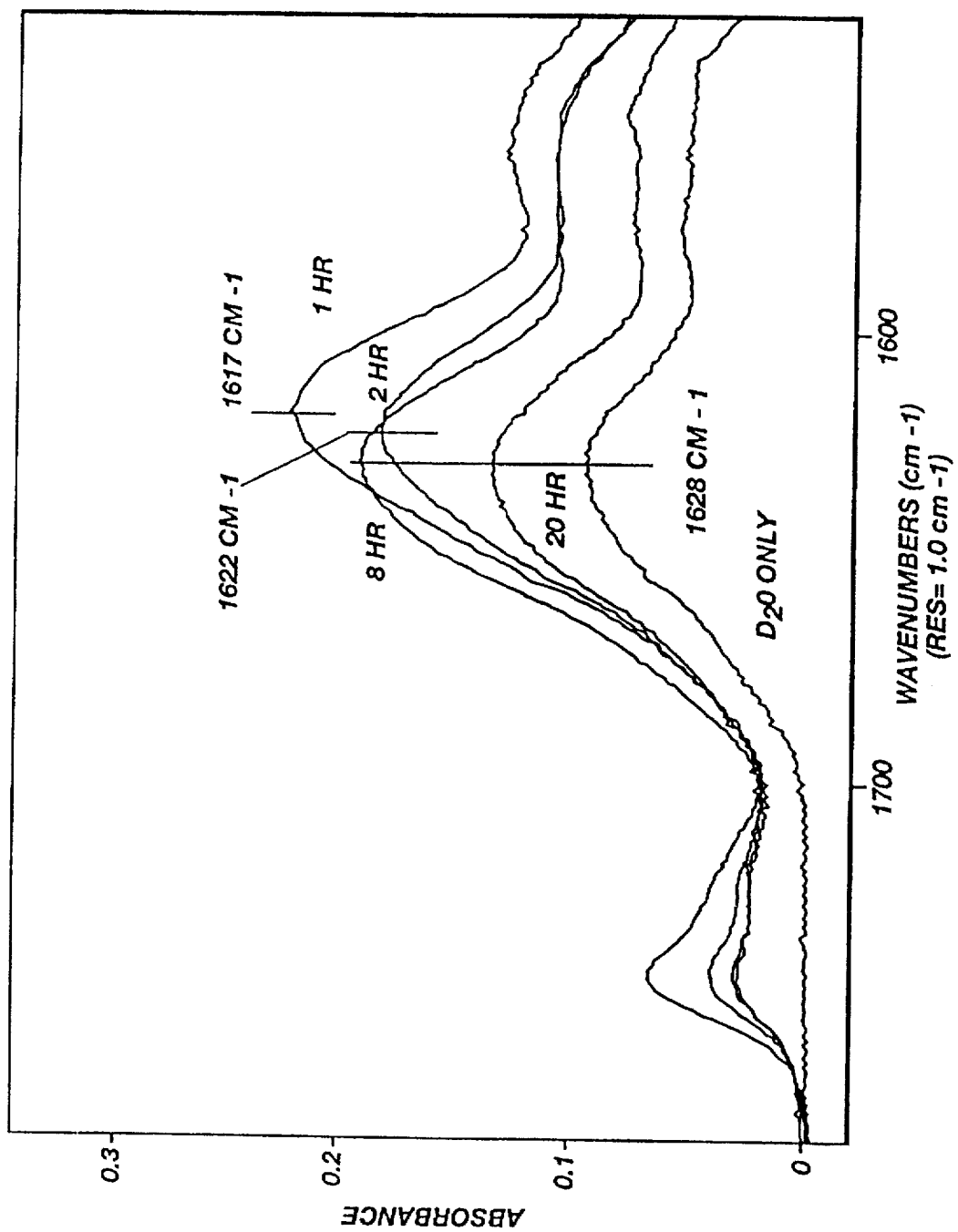
FIG. 5 is an absorbance spectrum of a human toe nail sample to which was applied a four milligram amount of a proteolytic enzyme composition.
Figure 6:
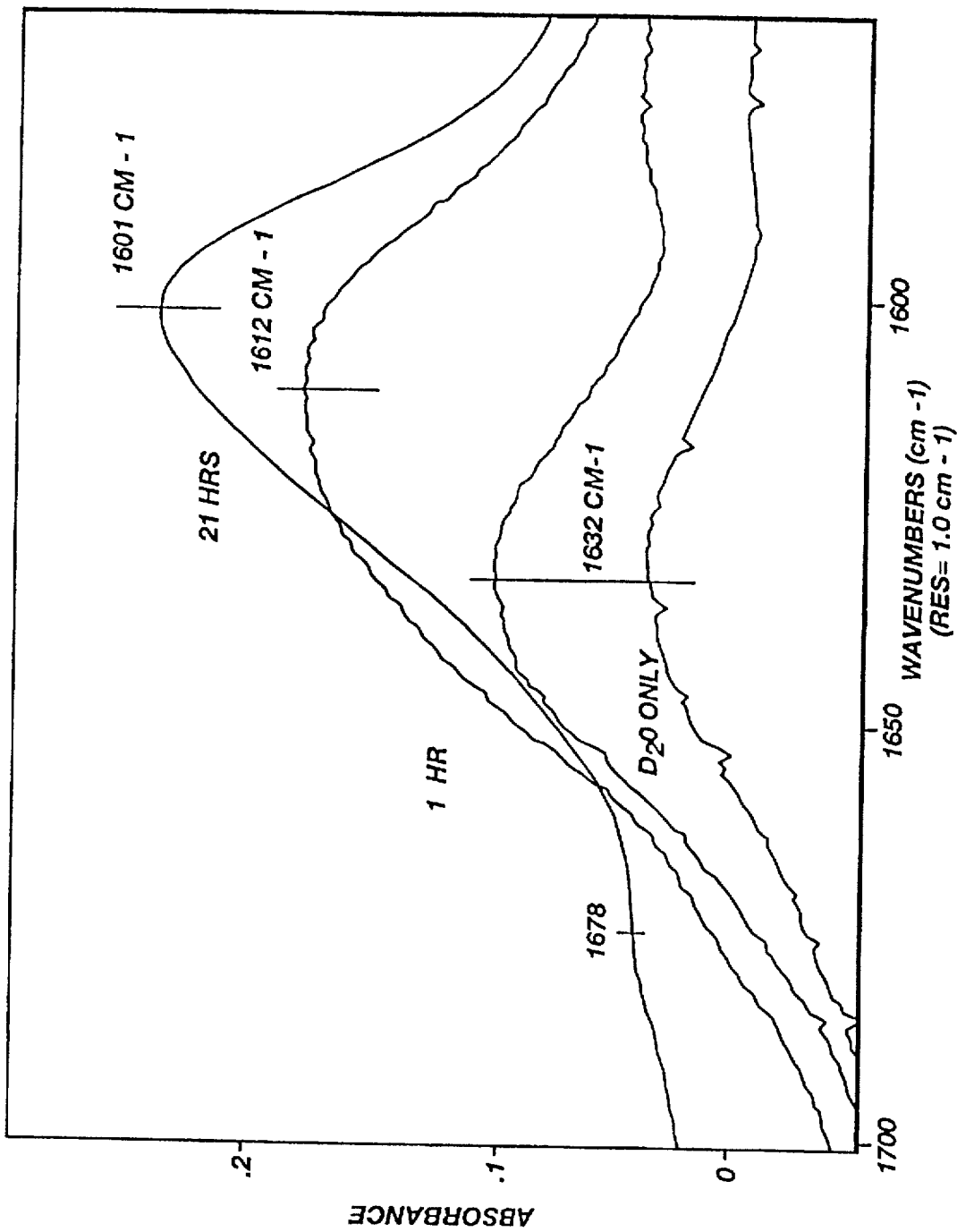
FIG. 6 is an absorbance spectrum of a human toe nail sample to which was applied a four molar (4M) solution of urea.

FIG. 5 illustrates another spectrum of a nail which was hydrated for three hours with heavy water and was then contacted with a thin film of four milligrams of the same proteolytic enzyme composition previously described. Scanning took place over a twenty hour period with the results that a band shift to lower wavelength values was observed within one to two hours following application with an eventual shift back to the original wavelength value at twenty hours. The affect of 4 molar urea (which is at substantially higher concentration than in the present composition) on toe nails hydrated for three hours in heavy water, as illustrated in FIG. 6, resulted in a significant band shift toward higher wave numbers. Both papain and urea appear to cause a further modification of the protein conformational populations than with urea alone, or in bonding configurations, which allows movement of drug molecules through the nail.

The proteolytic enzyme component of the nail-permeable medication means may contain from about 0.1 percent to about fifteen percent by weight of an enzyme, with a preferred amount being from six percent to ten percent by weight. The amount of proteolytic enzyme that is effective in the proteolytic enzyme component is affected to some degree by the activity of the proteolytic enzyme which is used in the composition. With respect to papain, for example, the activity of the enzyme may vary from source to source, and may be measured by different units of activity depending upon where the papain is purchased from or who the manufacturer is.

The United States Pharmacopeia (USP) has developed one standard of unit measurement of papain activity where one (1) USP Unit of papain activity is the activity which releases the equivalent of 1 µg (microgram) of tyrosine from a specified casein substrate under the conditions of the assay, using the enzyme concentration that liberates 40 µg of tyrosine per ml (milliliter) of test solution. USP papain contains at least 6,000 USP units per mg of papain. By contrast, for example, the Rystan Pharmaceutical Company, manufacturer of Panafil®, an enzyme-containing material (papain), has established its own activity measurement of papain. One Rystan Unit is that quantity which under specified conditions will clot 10 microliters of milk substrate in one minute at 40° C. Rystan Panafil®-White ointment is indicated as having 10,000 Rystan Units of enzyme activity per milligram of ointment. The Rystan Pharmaceutical Company reports that its product has the equivalent of 521.7 USP Units of activity.

Still other manufacturers, such as Sigma (Gaithersburg, Md.), indicates that its papain product contains approximately eighty percent (80%) protein and has an activity of 10–20 BAEE Units per milligram of enzyme-containing material. One BAEE Unit is defined as the quantity of papain that will hydrolyze 1.0 micromoles of BABE (N-α-benzoyl-L-argenine ethyl ester) per minute at 25° C. and pH 6.2. The ICN Company (Costa Mesa, Calif.) has three forms of papain available, one being 2× crystallized powder containing 10–20 BAEE Units of activity, the second being a 2× crystallized suspension form containing 15–40 BAEE Units and the third being a papain crude latex containing 1,750 USP Units/mg. No known means of correlating these activities is known to the inventors.

In formulating an exemplar proteolytic enzyme component, crude papain latex (uncut), typically containing 40,000 to 60,000 USP Units of activity per milligram, was dissolved in water and precipitated/crystallized by drop wise addition of ethanol, coupled with refrigeration, to isolate crystalline papain from the latex. Approximately thirty-three percent (33%) of the crude latex was converted into a crystalline/amorphous mixture, and from that it was estimated that approximately 20–25% yield of crystalline papain could be recovered from uncut papain latex upon 2× crystallization.

A particularly suitable formulation of the proteolytic enzyme component of the nail-permeable medication means is the following:

EXAMPLE I

| INGREDIENT | % BY WT. |
|---|---|
| Urea | 10.0 |
| Papain[1] | 6.0 |
| Glyceryl Sterate, PEG-150 Stearate | 3.1–4.5 |
| Cetyl Alcohol | 2.4–3.5 |
| Stearic Acid | 2.4–3.5 |
| Isopropyl Myristate | 6.3–9.0 |
| Dimethicone | 0.1–0.2 |
| Stearyl Alcohol | 1.9–2.8 |
| Boric Acid | 51.4–61.3 |
| Sodium Borate | 0.8–1.0 |
| Propylene Glycol | 4.2–6.0 |
| Triethanolamine | 0.2–0.3 |
| Phenoxyethanol, methylparaben, ethylparaben, propylparaben butylparaben (Phenonip)1.5 | 0.7–1.0 |

[1]Marcor Company (Hackensack, N.J.) papain having 30,000 USP Units/mg activity.

The foregoing formula for a proteolytic enzyme contains urea which has been demonstrated to enhance permeation of the skin. In a proteolytic enzyme component formulation including urea, the concentration of urea may be as high as 40% or greater, but is preferably in the range of 10% to 20%.

The medicament component of the nail-permeable medication means may contain any type of drug or medicament which is necessary and effective at modifying, controlling or curing a disease condition of the nail and the surrounding area. Such medicaments may include anti-bacterial compositions, anti-mycotic or antifungal compositions, antiviral compositions, or any other suitable medicament. Exemplar medicaments which are useful in the nail-permeable medication means are ciclopirox olamine, miconazole, itraconazole, clotrimazole, bifonazole, terbinafine, amorolfin, griseofulvin, econazole, tolnaftate and mixtures thereof. Effective amounts of these medicaments in the nail-permeable medication means will vary depending upon the disease condition to be treated. However, for most disease conditions, particularly fungal diseases, the minimum amount of medicament which will inhibit the growth or activity of a fungus (e.g., *Trichophyton rubrum* or *Trichophyton mentagrophytes*) is in the range of about 0.007 micrograms per milliliter to about 10 micrograms per milliliter. Specifically, for example, the minimum inhibitory concentration (MIC) of ciclopirox olamine with respect to *T. rubrum* is 10 µg/ml.

The efficacy of the nail-permeable medication means of the present invention was first evaluated by conducting comparative studies comprising application of a selected drug applied to a human nail in vitro as compared to the application of the nail-permeable medication means containing the same drug applied to a human nail in vitro. Specifically, these tests were conducted using diseased human toenails which were surgically removed from patients as a means of curing the disease condition of the nail.

Each nail was maintained in an environment simulating an in vivo condition. Each nail was maintained suspended on a plastic holder which allowed air to circulate about the nail. Each nail holder was retained in a separate enclosed system the temperature and humidity within which could be carefully regulated to simulate the human body. These artificial in vivo environments provided the diffusion cells in which the studies were conducted.

Figure 7:
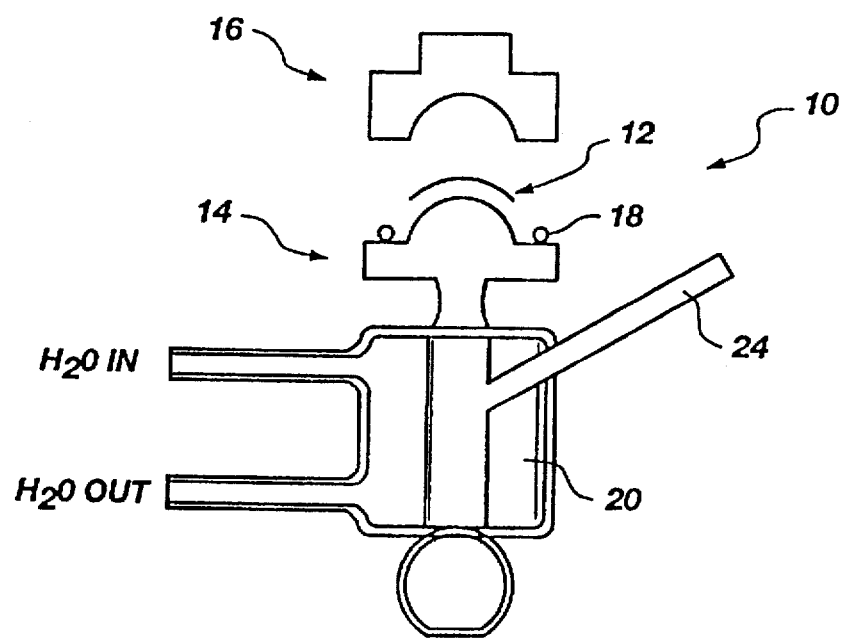
FIG. 7 is a representational illustration of a diffusion cell in which human nails may be maintained in a simulated in vivo environment.

Human nails were prepared by cleaning and, in some instances, grinding the nail down to establish a more even thickness across the nail. The nails were then hydrated using distilled water to render the nails pliable for placement in the diffusion cell. The prepared and hydrated nails were placed into nail diffusion cells 10, as illustrated in FIG. 7, by positioning the nail 12 over the nail saddle 14. A Teflon® donor compartment 16 was positioned over the nail 12 and the nail saddle 14 was joined to the donor compartment 16 by placement of a silicone sealant about the edges of the nail 12 and donor compartment 16. After the silicone cured, water leakage was tested and the nails were resealed if necessary. Care was taken in the application of the sealant to ensure that this material did not ooze into the nail absorption area as it was being clamped into place. Attempts were made to use an appropriate size "O" ring 18 to form the seal between the nail saddle 14 and the donor compartment 16.

Figure 8:
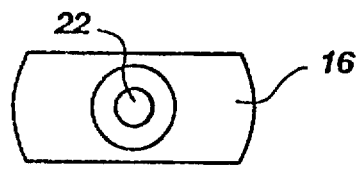
FIG. 8 is a plan view of the donor compartment illustrated in FIG. 7.

The cell 10 was used by adding solvent, usually de-ionized water, until the solvent came into contact with the nail. Fluid pre-treatment or treatment products were dropped into the port 22 of the donor compartment 16 as shown in FIG. 8, which illustrates a top view of the donor compartment 16. When semi-solid treatment formulations were used, excess product was removed from the nail by cleansing with cotton swabs after twenty-four hours and prior to application of another nail treatment or pre-treatment product. Pretreatment products (e.g., hydrating fluid, etc.) and treatment products (i.e., nail-permeable medication means) were changed or supplemented daily throughout the experimental period.

After addition of the pretreatment or treatment product, the opening of the donor cell 10 was occluded with silicone cement/sealant. The possibility of entrapped air at the interface of the receiver solvent and nail was checked daily, as well as at the beginning of the experiment. To control this problem, care was taken to be certain that no bubbles were present at the time solvents were added and the nail placed in the saddle. Bubbles may not be visible after the apparatus is fully assembled. Also, dissolved gases tend to separate into bubbles and rise to the nail/receiver interface during the process. It was found that tipping the apparatus into a horizontal position and tapping the cell gently did not interfere with the stirring or diffusion process and allowed the bubbles to escape through the sampling port 24.

Ciclopirox olamine (6-Cyclohexyl 1-hydroxy 4-methyl 2(1H)-pyridone, 2-aminoethanol salt [Bertrafen]), an antimycotic drug, was used in the nail-permeable medication means of the invention for the purposes of testing and analysis. Three analytical methods are identified in the literature which appear to be acceptable means of determining drug diffusion rates. One method requires the use of radio-labeled drug, and another method utilizes LC (liquid chromatography) equipment. The third method, described by Belliardo, et al., in "Micro-liquid chromatography method for the determination of ciclopirox olamine after pre-column derivatization in topical formulations" *Jr. Chromatography*, Vol. 553 (1991), p. 41–5, was the method used here. However, because of lack of access to a micro-LC system, lesser concentrations of ciclopirox olamine (<1–2 µg/ml of diffusion fluid) were unquantifiable. Lesser concentrations were sometimes seen as small irregularities on the HPLC (high-pressure liquid chromatography) tracing, but the identity was not confirmed by computer. In each analysis, from 1–3 ml of the nail-permeable medication means, as described further below, in substantially fluid form, was lyophilized and used for derivatization and analyses. The volume lyophilized depended on anticipated concentrations of ciclopirox olamine. Other quantities and volumes as reported in the publication were the same as used by the authors of the Belliardo article.

Figure 9:
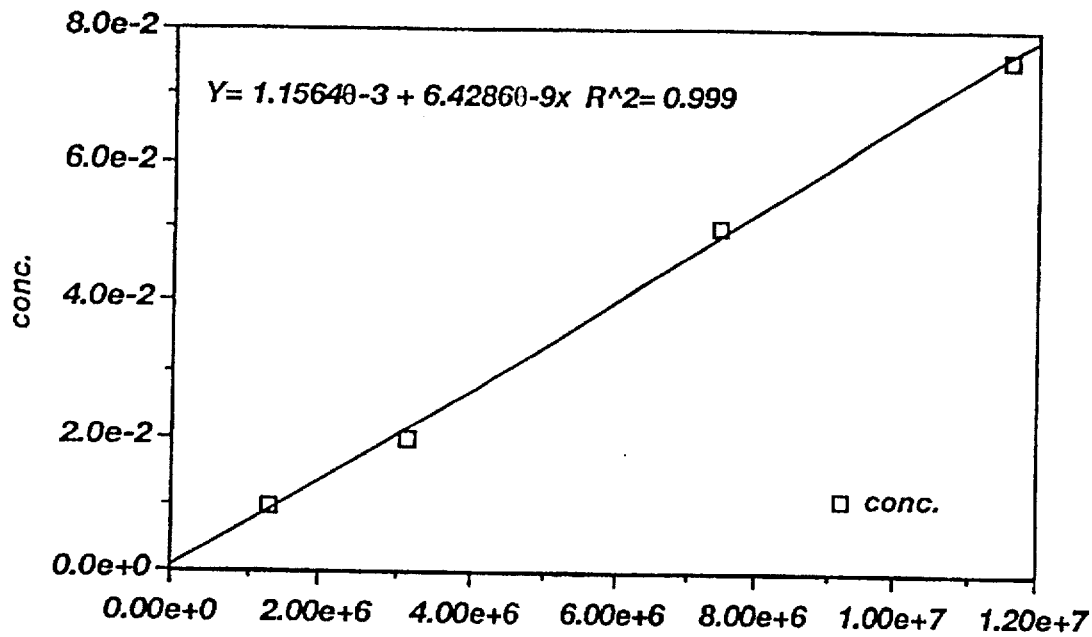
FIG. 9 is a standard calibration curve for ciclopirox olamine.
Figure 10:
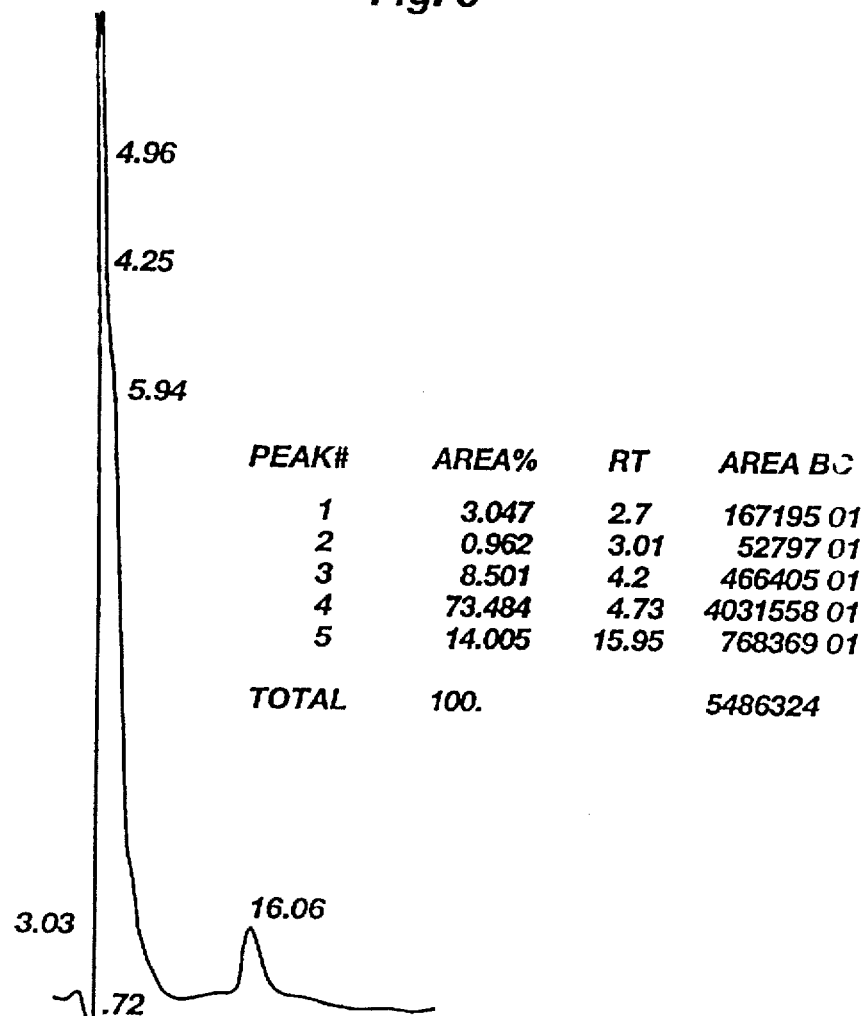
FIG. 10 is a standard ciclopirox olamine chromatographic peak.
Figure 13:
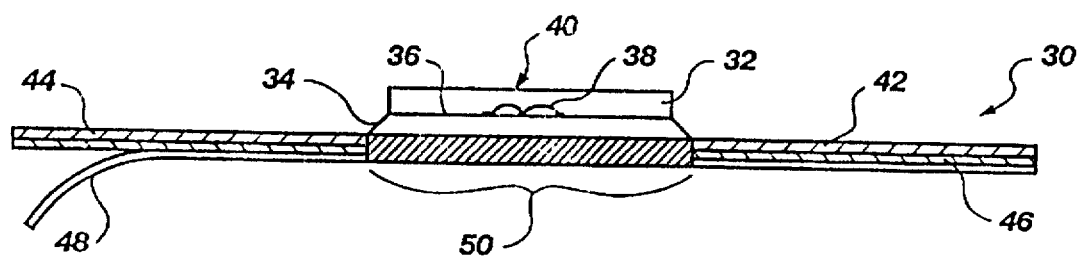
FIG. 13 is a view in cross section of an exemplary device for mixing the disclosed composition and occluding the wearer's skin after application.

Computer-generated calibration curves were obtained prior to each run using a standard solution prepared as described by Belliardo. A standard calibration curve is shown in FIG. 9 and a standard ciclopirox olamine peak is shown in FIG. 10. A computer-identified and quantified sample peak is shown in FIG. 11, and an unidentified peak in the expected location is shown in FIG. 12.

The nail-permeable medication means of the invention was prepared by formulating a proteolytic enzymatic component and a medicament component. The proteolytic enzyme component was prepared by making a composition containing a proteolytic enzyme and other additives. Papain was used in the proteolytic enzyme component of the nail-permeable medication means in all of the experiments. However, other proteolytic enzymes, such as bromelain and chymotrypsin are suitable for use in the invention. In most experiments, the concentration of papain was 0.5% Sigma papain (Sigma Co., product no. P4762 [2× crystallized, lyophilized powder, 16–20 BAEE units/mg]). Several experiments were conducted in which other concentrations (0.1%, 0.25% and 1.0%) of papain were used. In most studies, the 0.5% concentration papain produced optimal diffusion results.

Papain solutions also contained the activators l-cysteine (Sigma Co., product C-7755 [crystalline]) in a concentration of 0.28% and EDTA (Sigma Co. product EDS) in a concentration of 0.24%. All solutions were prepared fresh daily due to the instability of papain when dissolved in the activators. Unused portions of solutions were discarded if not used within one or two hours after preparation. Solutions were prepared by simple solution in water or mixtures of water and ethanol, although other alcohols may be substituted, including isopropyl. Most experiments were conducted using water alone as the solvent without buffering. In a few experiments, ethanol was mixed with water in 25:75 and 50:50 ratios. Some experiments also used buffered solutions. Buffering was accomplished with known phosphate buffers adjusted to pH 4.0, 7.4 and 10.0. In some later experiments a commercial form of papain (Panafil® Ointment, Rystan Co.) was used where papain concentrations were expressed in terms of USP units. The commercially available form of papain, Panafil®, contains 521 USP units of papain per mg of product.

Most experiments were conducted using 1.0% weight per volume of ciclopirox olamine (Sigma Company) dissolved in water or in ethanol/water mixtures in a ratio of 25:75 or 50:50. In some experiments, commercial forms of ciclopirox olamine were used. These included Loprox® from Hoechst-Roussel Company, in both lotion and cream forms. The enzyme component and drug component were combined at a ratio of about 50:50.

Some of the experiments were conducted by saturating felt pads with a papain solution including activators, as described above. The pads were immediately lyophilized (freeze dried) after soaking. In some of the experiments, a solution of papain without activators was also prepared and used to saturate pads which were lyophilized immediately. When lyophilized pads were used in the experiments, they were hydrated immediately preceding application of the pad to the nail.

SUMMARY OF IN VITRO STUDIES

The initial diffusion studies evaluating the nail-permeable medication means of the invention used papain (0.5% Sigma papain, product no. P4762) as the proteolytic enzyme and ciclopirox olamine as the medicament component. The diffusion studies were carried out by soaking the human nails in a 0.5% papain-plus-activators solution for 24 hours before placing them in the nail diffusion cells and measuring drug diffusion. As soaking time was increased from one day to three days, the amount of drug that diffused through the treated nails also increased. The papain-plus-activators, as well as the ciclopirox olamine drug, were dissolved in distilled water. Hydroalcoholic solutions as a solvent for the drug were also tried. The overall effect of these changes was that increasing soaking time of the proteolytic enzyme component containing papain-plus-activators, and the inclusion of an alcohol, such as ethanol in a concentration of at least twenty-five percent, in the solvent for the drug increased the amount of drug that diffused through the nailplate (ranges of 2–6 µg/ml increased to 3–9 µg/ml in a seven-day diffusion period). Control studies in which the nails were not contacted with any proteolytic enzyme component showed no diffusion of drug through the nail after seven (7) days of treatment, as determined by HPLC analyses. Solvents used for these studies included water, 25% ethanol in water and 50% ethanol in water.

Because it is impossible to soak toenails in clinical use, the proteolytic enzyme component containing papain-plus-activators was added to the diffusion cells on top of the nails as a solution for three days, after which the diffusion of the drug was measured for seven days (sample nos. 53–90). The amount of drug diffused was less than when the nails were soaked with the papain-plus-activators. It was also observed that the presence of alcohol in the solution for the drug increased drug diffusion for the seven-day period (ranges of 2–6 µg/ml). Increasing the concentration of the papain did not increase the amount of drug diffused.

In another group of tests (sample nos. 91–118), felt pads were used for papain as well as drug application to the nails. In some cases the pads were soaked with the solutions and used in that form. In other tests (sample nos. 119–154), the pads were saturated with the solution and then lyophilized before use. The use of saturated pads as a three-day pre-treatment and seven-day drug diffusion gave the best results (0.514 4 µg/ml). Several combinations of differing papain concentrations as well as methods and applications were tried using lyophilized pads. The inclusion of papain, activators and drug all in the same pad was tried (sample nos. 168, 169). The most successful method was that in which 0.5% Sigma papain and 1% drug in a lyophilized pad was hydrated with a solution containing activators after the pad was placed on the nail. Concentrations of diffused drug over a 21-day period were 1–3 µg/ml.

The results of the various tests conducted with the proteolytic enzyme component and the medicament component are shown in Table 1, as follows:

TABLE 1

| | PAPAIN | | | | CICLOPIROX | | | | |
|---|---|---|---|---|---|---|---|---|---|
| SAMPLE NO. | CONC. % | SOLVENT | MODE | DURA- TION | CONC. % | SOL- VENT | MODE | DURA- TION | ANALYSES (ug/ml) |
| 53 | 0.5 | W | S | 1D | 1 | W | T | 7D | 7 |
| 54 | 0.5 | W | S | 1D | 1 | W | T | 7D | 2 |
| 55 | 0.5 | W | S | 1D | 1 | W | T | 7D | 0 |
| 56 | 0.5 | W | S | 1D | 1 | 50A | T | 7D | <.3 |
| 57 | 0.5 | W | S | 1D | 1 | 50A | T | 7D | <.3 |
| 58 | 0.5 | W | S | 1D | 1 | 50A | T | 7D | 0 |
| 62 | 0.5 | W | S | 1D | 1 | 25A | T | 7D | 2 |
| 63 | 0.5 | W | S | 1D | 1 | 25A | T | 7D | 4 |
| 64 | 0.5 | W | S | 1D | 1 | 50A | T | 7D | 2 |
| 65 | 0.5 | W | S | 1D | 1 | 50A | T | 7D | 2 |
| 66 | 0.5 | W | S | 1D | 1 | 50A | T | 7D | 1 |
| 67 | 0.5 | W | S | 1D | 1 | 50A | T | 7D | 0 |
| 68 | 0.5 | W | S | 1D | 1 | 25A | T | 7D | 0 |
| 69 | 0.5 | W | S | 1D | 1 | 25A | T | 7D | 5 |
| 70 | 0.5 | W | S | 1D | 1 | 25A | T | 7D | 2 |
| 71 | 0.5 | W | S | 1D | 1 | 25A | T | 7D | 0 |
| 72 | 0.5 | W | S | 1D | 1 | 25A | T | 7D | <.3 |
| 73 | 0.5 | W | S | 2D | 1 | W | T | 7D | 4 |
| 74 | 0.5 | W | S | 2D | 1 | W | T | 7D | 2 |
| 75 | 0.5 | W | S | 2D | 1 | W | T | 7D | 0 |
| 76 | 0.5 | W | S | 2D | 1 | 25A | T | 7D | 6 |
| 77 | 0.5 | W | S | 2 | 1 | 25A | T | 7D | 3 |
| 78 | 0.5 | W | S | 2D | 1 | 25A | T | 7D | <.3 |
| 79 | 0.5 | W | S | 2D | 1 | 50A | T | 7D | <.3 |
| 80 | 0.5 | W | S | 2D | 1 | 50A | T | 7D | <.3 |
| 81 | 0.5 | W | S | 2D | 1 | 50A | T | 7D | 4 |
| 82 | 1 | W | S | 1D | 1 | W | T | 7D | 7 |
| 83 | 1 | W | S | 1D | 1 | W | T | 7D | 3 |
| 84 | 1 | W | S | 1D | 1 | W | T | 7D | <.3 |
| 85 | 0.5 | W | S | 1D | 1 | 50A | T | 7D | 4 |
| 86 | 0.5 | W | S | 1D | 1 | 50A | T | 7D | 3 |
| 87 | 0.5 | W | S | 1D | 1 | 50A | T | 7D | 3 |
| 88 | 2 | W | S | 1D | 1 | 50A | T | 7D | <.3 |
| 89 | 2 | W | S | 1D | 1 | 50A | T | 7D | <.3 |
| 90 | 2 | W | S | 1D | 1 | 50A | T | 7D | <.3 |
| 91 | 0.5 | W | FP* | 2D | 1 | W | FP* | 7D | <.3 |
| 92 | 1 | W | FP | 2D | 1 | W | FP | 7D | 0 |
| 93 | 1 | W | FP | 2D | 1 | W | FP | 7D | 0 |
| 94 | 0.1 | W | FP | 1D | 1 | 50A | T | 7D | 0 |
| 95 | 0.1 | W | FP | 1D | 1 | 50A | T | 7D | 0 |
| 96 | 0.25 | W | FP | 1D | 1 | 50A | T | 7D | <.3 |
| 97 | 0.25 | W | FP | 1D | 1 | 50A | T | 7D | <.3 |
| 98 | 1 | W | FP | 2D | 1 | 50A | FP | 7D | <.3 |
| 99 | 1 | W | FP | 2D | 1 | 50A | FP | 7D | <.3 |
| 100 | 1 | W | FP | 2D | 1 | 50A | FP | 7D | <.3 |
| 101 | 0.5 | W | FP | 3D | 1 | 25A | FP | 7D | <.3 |
| 102 | 0.5 | W | FP | 3D | 1 | 25A | FP | 7D | 1 |
| 103 | 0.5 | W | FP | 3D | 1 | 25A | FP | 7D | 2 |
| 104 | 0.5 | W | FP | 3D | 1 | 50A | FP | 7D | 0 |
| 105 | 0.5 | W | FP | 3D | 1 | 50A | FP | 7D | 4 |
| 106 | 2 | W | FP | 3D | 1 | 50A | FP | 7D | 4 |
| 107 | 2 | W | FP | 6D | 1 | W | FP | 7D | 1 |
| 108 | 2 | W | FP | 6D | 1 | W | FP | 7D | 0 |
| 109 | 0.5 | W | FP | 6D | 1 | W | FP | 7D | 2 |
| 110 | 0.5 | W | FP | 3D | 1 | W | FP | 7D | 1 |
| 111 | 0.5 | W | FP | 3D | 1 | W | FP | 7D | 34** |
| 112 | 0.5 | W | FP | 3D | 1 | 25A | FP | 7D | 1 |
| 113 | 0.5 | W | FP | 3D | 1 | 25A | FP | 7D | 3 |
| 114 | 0.5 | W | FP | 3D | 1 | 50A | FP | 7D | 3 |
| 115 | 0.5 | W | FP | 3D | 1 | 50A | FP | 7D | 2 |
| 116 | 0.5 | W | FP | 3D | 1 | 50A | FP | 7D | 0 |
| 117 | 0.5 | W | FP | 3D | 1 | 50A | FP | 7D | 0 |
| 118 | 0.5 | W | FP | 3D | 1 | 50A | FP | 7D | 0 |
| 119 | 0.5 | W | LFP | 3D | 1 | W | LFP | 7D | 0*** |
| 120 | 0.5 | W | LFP | 3D | 1 | W | LFP | 7D | 0*** |
| 121 | 0.5 | W | LFP | 3D | 1 | W | LFP | 7D | 0*** |
| 122 | 0.5 | W | LFP | 3D | 1 | W | LFP | 7D | 0*** |
| 123 | 0.5 | W | LFP | 3D | 1 | W | LFP | 7D | 0*** |
| 124 | 0.5 | W | LFP | 3D | 1 | W | LFP | 7D | 0*** |
| 128 | 0.5 | W | LFP | 3D | 1 | W | LFP | 7D | 0**** |
| 129 | 0.5 | W | LFP | 3D | 1 | W | LFP | 7D | 0**** |
| 130 | 0.5 | W | LFP | 3D | 1 | W | LFP | 7D | 0**** |

TABLE 1-continued

| | PAPAIN | | | | CICLOPIROX | | | | | |
|---|---|---|---|---|---|---|---|---|---|---|
| SAMPLE NO. | CONC. % | SOLVENT | MODE | DURA-TION | CONC. % | SOL-VENT | MODE | DURA-TION | ANALYSES (ug/ml) | COMMENTS |
| 131 | 0.5 | W | LFP | 3D | 1 | W | FP | 7D | 0 | |
| 132 | 0.5 | W | LFP | 3D | 1 | W | FP | 7D | 0 | |
| 133 | 0.5 | W | LFP | 3D | 1 | W | FP | 7D | 0 | |
| 140 | 0.1 | W | LFP | 3D | 1 | W | FP | 7D | 1 | Activators added in hydration fluid |
| 141 | 0.1 | W | LFP | 3D | 1 | W | FP | 7D | 1 | Activators added in hydration fluid |
| 142 | 0.1 | W | LFP | 3D | 1 | W | FP | 7D | <.3 | Activators added in hydration fluid |
| 143 | 0.1 | PG | LFP | 3D | 1 | W | FP | 7D | 0 | Propylene glycol as hydration fluid (pap) |
| 144 | 0.1 | PG | LFP | 3D | 1 | W | FP | 7D | 0 | Propylene glycol as hydration fluid (pap) |
| 145 | 0.1 | PG | LFP | 3D | 1 | W | FP | 7D | 0 | Propylene glycol as hydration fluid (pap) |
| 146 | 0.1 | PG | LFP | 3D | 1 | W | LFP | 7D | 0 | Propylene glycol as hydration fluid (pap) Not occl. |
| 147 | 0.1 | PG | LFP | 3D | 1 | W | LFP | 7D | 0 | Propylene glycol as hydration fluid (pap) |
| 148 | 0.1 | PG | LFP | 3D | 1 | W | LFP | 7D | 0 | Propylene glycol as hydration fluid (pap) |
| 149 | 0.1 | W | LFP | 3D | 1 | 50A | LFP | 7D | 11.8 | 50A as hydration fluid for ciclopirox |
| 150 | 0.1 | W | LFP | 3D | 1 | 50A | LFP | 7D | 3 | 50A as hydration fluid for ciclopirox |
| 151 | 0.1 | W | LFP | 3D | 1 | 50A | LFP | 7D | 0 | 50A as hydration fluid for ciclopirox |
| 152 | 0.5 | W | LFP | 3D | 1 | 50A | FP | 30D | 2456 | 50A as hydration fluid for ciclopirox -Probable leakage |
| 153 | 0.5 | W | LFP | 3D | 1 | 50A | FP | 30D | 0.5 | 50A as hydration fluid for ciclopirox |
| 154 | 0.5 | W | LFP | 3D | 1 | 50A | FP | 30D | <.3 | 50A as hydration fluid for ciclopirox |
| 155 | 0.5 | W | FP | 3D | 1 | W | FP | 30D | 0.5 | Activators added in hydration fluid |
| 156 | 0.5 | W | FP | 3D | 1 | W | FP | 30D | <.3 | Activators added in hydration fluid |
| 157 | 0.5 | W | FP | 3D | 1 | W | FP | 30D | <.3 | Activators added in hydration fluid |
| 158 | 0.1 | W | FP | 3D | 1L | L | T | 20D | 0 | Activators added in hydration fluid |
| 159 | 0.1 | W | FP | 3D | 1L | L | T | 20D | 0 | Activators added in hydration fluid |
| 160 | 0.1 | W | FP | 3D | 1L | L | T | 20D | 0 | Activators added in hydration fluid |
| 161 | 0.1 | PG | FP | 3D | 1L | L | T | 20D | 0 | Activators added in hydration fluid |
| 162 | 0.1 | W | FP | 3D | 1L | L | T | 20D | 21.8 | Activators added in hydration fluid-Probable leakage. |
| 163 | 0.1 | W | FP | 3D | 1L | L | T | 20D | 0 | |
| 170 | P | P | T | 3D | 1L | L | T | 7D | 0 | |
| 171 | P | P | T | 3D | 1L | L | T | 7D | 0 | |
| 172 | P + W | P + W | T | 3D | 1L | L | T | 7D | 0 | |
| 173 | P + W | P + W | T | 3D | 1L | L | T | 7D | 0 | |
| 174 | P + A | P + A | T | 3D | 1L | L | T | 7D | 0 | |
| 175 | P + A | P + A | T | 3D | 1L | L | T | 7D | 0 | |
| 164 | P | P | FP | 3D | 1L | L | T | 40D | 0 | |
| 165 | P | P | FP | 3D | 1L | L | T | 40D | 0 | |
| 166 | P | P | FP | 3D | 1L | L | T | 40D | 0 | |
| 167 | P | P | T | 6D | 1L | L | T | 40d | 0 | Activators added in hydration fluid |
| 168 | P + L | P + L | T | 46D | P + L | P + L | T | 46D | <.3 | Panafil and Loprox used together on nails |
| 169 | P + L | P + L | T | 46D | P + L | P + L | T | 46D | <.3 | Panafil and Loprox used together on nails |
| 176 | 0.5 | pH10 | S | 5D | 1 | W | T | 10D | 0 | |
| 177 | 0.5 | pH10 | S | 5D | 1 | W | T | 10D | 0 | |
| 178 | 0.5 | pH10 | S | 5D | 6 | W | T | 10D | 250 | Probably a leaker. |
| 179 | 0.5 | pH10 | S | 5D | 6 | W | T | 10D | 30 | Probably a leaker. |
| 180 | 0.5 | pH4 | S | 5D | 1 | W | T | 10D | 0 | |
| 181 | 0.5 | pH4 | S | 5D | 1 | W | T | 10D | 75 | Probably a leaker. |
| 182 | 0.5 | pH4 | S | 5D | 6 | W | T | 10D | 10 | |
| 183 | 0.5 | pH4 | S | 5D | 6 | W | T | 10D | 0 | |

*In experiments using felt pads, the pads were changed on a daily basis.
**Result may be due to leakage.
***No activators in papain solution.
****Activators added in hydration fluid (pap).
KEY
W = Water
S = Soak
D = Days
L = Loprox Cream, 1.0%
T = Topical application on nail
FP = Felt Pad
PG = Propylene Glycol
50A = 50% Alcohol in water
25A = 25% Alcohol in water
LFP = Lyophilized felt pads
P + W = Panafil and water mixed, 50% each
P + A = Activators (EDTA & Cysteine) added to Panafil Ointment
<.3 = Concentration less than 0.3 µg/ml, etc. Small blip, below HPLC ability to identify and quantify.

RESULTS OF CLINICAL STUDIES

A pilot clinical study was conducted by investigators in Salt Lake City, Utah and Miami, Fla. consisting of approximately fifty patients who had onychomycosis. Patients enrolled in the study were diagnosed with subungual onychomycosis from a positive culture of a target nail. The target nail was that nail most severely involved with symptoms of onychomycosis. While the majority of patients included had previously received topical therapies for their onychomycosis, patients treated with other topical antifungals within 14 days, or systemic treatments within six months prior to study entry, were excluded from the study. Patients with a history of non-response to standard antimycotic treatments, or severe abnormalities or deformities of the assessed fingers or toes, were excluded. Also, patients who had demonstrated previous intolerance to either the antifungal agent or other proteolytic enzymes, who had vascular compromise of their extremities, or had intrinsic nail disease were excluded.

Patients chosen for the study were randomly placed into one of the four study arms shown in Table 2. The protocol called for an eleven month treatment period.

TABLE 2

| ARM | APPLICATION |
|---|---|
| 1 | Proteolytic enzyme[1] pre-treatment for 2 weeks followed by antifungal[2] treatment B.I.D. |
| 2 | Concurrent, B.I.D. treatment with nail-permeable medication means[3] |
| 3 | B.I.D. treatment with antifungal[2] alone |
| 4 | Concurrent Q.D. treatment with nail-permeable medication means[3] |

[1] The enzyme used for the studies was the formula described in EXAMPLE I, above.
[2] The antifungal medicament used in the studies was ciclopirox olamine in a concentration of 1%.
[3] The nail-permeable medication means used in this study was a preparation containing the proteolytic enzyme component described in EXAMPLE I in admixture with ciclopirox olamine in a concentration of about 10 mg/ml in a ratio of about 50:50.

Patients visited their physicians on a monthly basis for evaluation. Clinical measurements and mycological cultures were taken on alternating visits. Adverse events were defined as any abnormal inflammation of the tissues surrounding the nail from the patient's pretreatment condition and were checked by their physician or reported as they occurred. Patient evaluations of clinical treatment were obtained by a survey of patients. Ease of application, convenience of application, and patient's assessments of the clinical results were rated by patients on a scale of 1 to 5 with 1 indicating visible effect and 5 being positive. In addition, patients were also asked to respond to treatment compliance by reporting the number of days per week which they applied their medication as prescribed.

Due to previously reported high relapse rates of onychomycosis among other investigators' studies, a follow-up study was conducted with patients from this pilot clinical study who achieved clinical cure. Patients with clinical cure (target nail 100% clear of fungus following treatment) were randomly placed into one of two follow-up arms of the study as follows:

1. One-third of the patients received no treatment for follow-up, yet continued to be observed for reoccurrence of fungus for a period of six months.
2. Two-thirds of the patients were asked to apply the medication according to the arm 4 treatment regime (single daily concurrent treatment using the permeation medicament) for one week per month, for a period of six months.

In addition to this follow-up, all failures from study arms 1 and 3 were moved into arm 4 where they were treated with a dose of the nail-permeable medication means on a once-per-day basis. Arm 2 (Table 3) patients, upon complete cure, were also entered into the follow-up study as outlined above.

Treatment of onychomycosis with topical antifungal agents has typically not resulted in either mycologic or clinical cure in the past. Therefore, patients treated in arm 3 (antifungal only) of the study were used as the baseline upon which clinical and mycologic results were measured.

Despite good compliance by patients whose toes were treated in arm 1 of the study (Table 3), an average growth rate of clear nail of approximately 1 mm was observed over the first four months of the trial. The lack of clear nail growth over this period of time may be due to the lack of treatment with the nail-permeable medication means following the initial two weeks of proteolytic enzyme component-only therapy. It was also observed that during the 2 week treatment of twice per day application of proteolytic enzyme component, adverse reactions occurred in approximately 73% of the patients.

Compliance was also good among patients whose toes were treated in arm 2, and the average growth was approximately 3 mm over the first four months of the trial. These results showed that the proteolytic enzyme component had a positive affect in assisting penetration. The mycologic cure rate in this group was approximately 71%. Unfortunately, the incidence of adverse reactions in this group was approximately 67%. This was presumably due to the twice daily application of the proteolytic enzyme component.

Patients treated in arm 3 (with antifungal only) felt that it was very convenient, yet they experienced no clear nail growth and either dropped out of the study due to a lack of result after five months or were switched to arm 4 of the study. This supports previous studies that suggest topical antifungal agents alone have minimal effect on either clinical or mycologic cure of onychomycosis. No adverse reactions were reported or observed in this patient population.

Patients in arm 4 showed excellent compliance, and also showed average clear growth rates of approximately 3 mm at month 4, 4.4 mm at month 5, and 6 mm at month 7. Patients treated in arm 4 received treatment to fingers. It should be noted that finger nails grow at a more rapid pace than do toe nails. Patients in arm 4 also showed a mycological cure rate of approximately 75% at month 7 and continued to show increased improvement as treatment continued. No adverse reactions were reported or observed in this patient population.

TABLE 3

| Study Arm | Clear Growth (4 mos.) | % Adverse Reactions | Average Days of Treatment Per Week | Ease of Use (1–5) | Convenience of Use (1–5) | Results (1–5) | % Cult. Neg. |
|---|---|---|---|---|---|---|---|
| 1 | 1 mm | 73 | 5.71 | 3.88 | 3.38 | 4.25 | — |
| 2 | 3 mm | 67 | 6.80 | 3.8 | 3.8 | 4.2 | 71 |
| 3 | 0 mm | 0 | 6.50 | 5 | 5 | 1 | — |
| 4 | 3.14 mm | 0 | 6.75 | 4.63 | 4.75 | 4.2 | 75 |

Preliminary clinical data and patient survey results are summarized in Table 3. These results suggest the following: First, the high incidence of adverse reactions in arms 1 and 2 of the study, as illustrated in Table 3, indicate that twice daily applications of the proteolytic enzyme component alone are not acceptable. Although none of the adverse reactions were severe, the high rate does interfere with patient compliance and interrupts the daily regime.

Second, all arms using the nail-permeable medication means (1, 2, and 4) show both clinical and mycological improvement. Because of the intensive application of the proteolytic enzyme component in the first two weeks in arm 1, there is an initial clear nail growth. However, patients in this arm slow, or regress, over time showing only an average 1 mm of clear nail growth at four months, as illustrated in Table 3. This is likely due to the terminated application of proteolytic enzyme component after two weeks. Clear growth in arms 2 and 4 continued to increase over time. Patients also reported high satisfaction with results in all arms using the proteolytic enzyme component.

Third, patients in all arms reported that the nail-permeable medication means was both easy to use and a convenient form of application. Patients involved in the once a day application in arm 4 reported higher satisfaction in the survey. In all arms patients reported very high compliance as summarized in Table 3. The overall average daily treatment rate was 6.4 days per week. Arm 4 reported application 6.75 days per week.

The results of the pilot study indicated that concurrent, once a day, treatment with the nail-permeable medication means (arm 4) appears to be both the safest and most effective regime for the treatment of onychomycosis. Although the patients in the clinical studies applied a preformed nail-permeable medication means comprising a proteolytic enzyme component and a medicament component, it has been observed that comparable success rates for treatment of onychomycosis has resulted where patients have combined equal portions of the proteolytic enzyme component and the medicament component immediately prior to application to the diseased nail. Further, comparable success rates have been demonstrated in patients who mixed equal portions of the proteolytic enzyme component and the medicament component directly on the nail surface and surrounding area. In all manners of application, patients applied occlusion means to the treated nail area following application of the nail-permeable medication means or proteolytic enzyme component and medicament component.

What is claimed is:

1. A nail-permeable composition for treatment of disease conditions in animal nails comprising a proteolytic enzyme component having an effective amount of proteolytic enzyme in a concentration of from about 0.1% to about 15% by weight of the applied composition to facilitate permeation through animal nails without causing debridement and a medicament component having an effective amount of disease-affecting medicament in admixture with said proteolytic enzyme component to form a topically spreadable composition.

2. The nail-permeable composition of claim 1 wherein said medicament is an antibacterial, antifungal, anti-viral or other anti-microbial drug.

3. The nail-permeable composition of claim 2 wherein said medicament is selected from the group consisting of ciclopirox olamine, miconazole, itraconazole, clotrimazole, bifonazole, terbinafine, amorolfin, griseofulvin, econazole, tolnaftate and mixtures thereof.

4. The nail-permeable composition of claim 3 wherein said medicament is ciclopirox olamine in a concentration of about 1 mg/ml to about 10 mg/ml.

5. The nail-permeable composition of claim 3 wherein said proteolytic enzyme is papain.

6. The nail-permeable composition of claim 5 wherein said proteolytic enzyme has a measured proteolytic activity equivalent to about 500 USP units/mg of enzyme to about 60,000 USP units/mg of enzyme.

7. The nail-permeable composition of claim 5 wherein said proteolytic enzyme has a measured proteolytic activity equivalent to about 10 BAEE units/mg of enzyme-containing material to about 40 BAEE units/mg of enzyme-containing material.

8. The nail-permeable composition of claim 5 wherein said proteolytic enzyme has a measured proteolytic activity equivalent to about 10,000 Rystan Units per milligram of enzyme-containing material.

9. The nail-permeable composition of claim 3 wherein said proteolytic enzyme component further comprises urea in a concentration of up to about twenty percent by weight.

10. The nail-permeable composition of claim 9 wherein said proteolytic enzyme component further includes proteolytic enzyme activators.

11. The nail-permeable composition of claim 10 further including alcohol.

12. The nail-permeable composition of claim 11 wherein said medicament component further contains ethanol up to about seventy percent by weight.

* * * * *

UNITED STATES PATENT AND TRADEMARK OFFICE
CERTIFICATE OF CORRECTION

PATENT NO : 5,840,283
DATED : November 24, 1998
INVENTOR(S) : Sorenson et al.

It is certified that error appears in the above-identified patent and that said Letters Patent is hereby corrected as shown below:

In column 1, line 16, after "hoof", insert a comma --,--;

In column 1, line 27, after "States", insert a comma --,--;

In column 1, line 28, after "40", insert a comma --,--;

In column 1, line 29, after "occur" insert a comma --,--;

In column 1, line 29, after "extent", insert a comma --,--;

In column 2, line 54, after "invention", insert a comma --,--;

In column 2, line 58, after "notable", insert a comma --,--;

In column 2, line 59, after "respect", insert a comma --,--;

In column 3, line 32, after "time", insert a comma --,--;

UNITED STATES PATENT AND TRADEMARK OFFICE
CERTIFICATE OF CORRECTION

PATENT NO : 5,840,283

DATED : November 24, 1998

INVENTOR(S) : Sorenson et al.

It is certified that error appears in the above-identified patent and that said Letters Patent is hereby corrected as shown below:

In column 5, line 33, after "nails", insert a comma --,--;

In column 6, line 31, after "quantity", insert a comma --,--;

In column 6, line 32, after "conditions", insert a comma --,--;

In column 7, line 22, after "urea", insert a comma --,--;

In column 7, line 38, after "vary", insert a comma --,--;

In column 7, line 51, after "vitro", insert a comma --,--;

In column 7, line 60, after "holder", insert a comma --,--;

In column 7, line 61, after "system", insert a comma --,--;

In column 7, line 62, after "within", insert a comma --,--;

In column 8, line 1, after "hydrated", insert a comma --,--;

In column 8, line 9, after "resealed", insert a comma --,--;

In column 8, line 18, after "16", insert a comma --,--;

In column 8, line 43, after "Bertrafen", insert a --®--;

In column 8, line 47, after "literature", insert a comma --,--;

UNITED STATES PATENT AND TRADEMARK OFFICE
CERTIFICATE OF CORRECTION

PATENT NO : 5,840,283
DATED : November 24, 1998
INVENTOR(S) : Sorenson et al.

It is certified that error appears in the above-identified patent and that said Letters Patent is hereby corrected as shown below:

In column 8, line 64, after "lyophilized", insert a comma --,--;

In column 8, lines 65-66, after "volumes", insert a comma --,--;

In column 8, line 66, after "publication", insert a comma --,--;

In column 9, line 2, after "prepared", insert a comma --,--;

In column 9, line 15, after "chymotrypsin", insert a comma --,--;

In column 9, line 26, after "daily", insert a comma --,--;

In column 9, line 37, after "experiments", insert a comma --,--;

In column 9, line 52, after "solution", insert a comma --,--;

In column 10, line 14, after "solutions", insert a comma --,--;

In column 10, line 15, after "drug", insert a comma --,--;

In column 10, line 42, after "cases", insert a comma --,--;

In column 10, line 48, after "concentrations", insert a comma --,--;

In column 10, line 48, after "applications", insert a comma --,--;

In column 15, line 1, after "nail", insert a comma --,--;

UNITED STATES PATENT AND TRADEMARK OFFICE
CERTIFICATE OF CORRECTION

PATENT NO : 5,840,283
DATED : November 24, 1998
INVENTOR(S) : Sorenson et al.

It is certified that error appears in the above-identified patent and that said Letters Patent is hereby corrected as shown below:

In column 15, line 45, after "5", insert a comma --,--;

In column 17, line 14, after "arms", insert a comma --,--.

Signed and Sealed this

Third Day of August, 1999

Attest:

Attesting Officer

Q. TODD DICKINSON

Acting Commissioner of Patents and Trademarks